United States Patent
Gupta et al.

(10) Patent No.: US 6,501,849 B1
(45) Date of Patent: *Dec. 31, 2002

(54) SYSTEM AND METHOD FOR PERFORMING IMAGE-BASED DIAGNOSIS OVER A NETWORK

(75) Inventors: Rajiv Gupta, New York, NY (US); Christopher James Daily, Ogden, UT (US); Rasiklal Punjalal Shah, Latham, NY (US); Valtino Xavier Afonso, DesPlaines, IL (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/474,499

(22) Filed: Dec. 29, 1999

Related U.S. Application Data

(63) Continuation-in-part of application No. 08/921,959, filed on Sep. 2, 1997, now Pat. No. 6,115,489.

(51) Int. Cl.$^7$ ................................................ G06K 9/00
(52) U.S. Cl. ........................ 382/141; 382/152; 382/157
(58) Field of Search .................................. 382/152, 157, 382/141; 348/86, 87, 130, 125, 126; 364/474.21, 474.34; 702/34, 35; 701/29, 30

(56) References Cited

U.S. PATENT DOCUMENTS

| | | | |
|---|---|---|---|
| 5,838,816 A | 11/1998 | Holmberg | 382/157 |
| 5,926,558 A | 7/1999 | Zelt, III et al. | 382/152 |
| 6,062,631 A | * 4/2000 | Busch et al. | 701/29 |
| 6,115,489 A | * 9/2000 | Gupta et al. | 382/141 |

* cited by examiner

*Primary Examiner*—Joseph Mancuso
*Assistant Examiner*—Vikkram Bali
(74) *Attorney, Agent, or Firm*—Foley & Lardner; Peter J. Vogel; Michael A. Della Penna

(57) ABSTRACT

A system for performing image-based diagnosis of a machine includes a database containing a plurality of historical images taken from a plurality of machines, a diagnostic unit configured to diagnose a new artifact image from the machine and to communicate historical and non-historical images or data associated with the system to a remote facility. The plurality of historical images include a plurality of ideal images generated from the plurality of machines using all possible machine settings and a plurality of artifact images generated from the plurality of machines, each of the artifact images having known faults associated therewith and a corresponding corrective action for repairing the faults. The diagnostic unit includes a diagnostic image processor and a diagnostic fault isolator. The diagnostic image processor includes means for finding an ideal image from the plurality of historical images that most closely matches the new artifact image, means for assigning an artifact category to the new artifact image based on the matched ideal image, and means for extracting an artifact feature from the new artifact image according to the assigned category. The diagnostic fault isolator includes means for generating a plurality of metrics for the extracted artifact feature and means for applying the plurality of metrics to identify an artifact image from the plurality of historical images that most closely matches the new artifact image and a corrective action for repairing the unknown fault.

21 Claims, 9 Drawing Sheets

SYSTEM AND METHOD FOR PERFORMING IMAGE-BASED DIAGNOSIS OVER A NETWORK

CROSS REFERENCE TO RELATED APPLICATIONS

This application is a continuation-in-part (CIP) of U.S. patent application Ser. No. 08/921,959 entitled "System And Method For Performing Image-Based Diagnosis" filed on Sep. 2, 1997 now U.S. Pat. No. 6,115,489.

BACKGROUND OF THE INVENTION

The present invention relates generally to the field of medical diagnostic systems, such as imaging systems. More particularly, the invention relates to a system and technique for quickly diagnosing a malfunction of a medical diagnostic system.

In either an industrial or commercial setting, a malfunctioning imaging machine can impair a business severely. Thus, it is essential that a malfunctioning imaging machine be repaired quickly and accurately. Usually, during a malfunction of an imaging machine such as an ultrasound, computed tomography (CT), or a magnetic resonance imaging (MRI) machine, a field engineer is called in to diagnose and repair the machine. Typically, the field engineer looks at an incident record generated from the machine. The incident record contains information such as the type of machine, the modality of the machine, and any customer-related information. In addition, the incident record contains an error log of events that occurred during routine operation as well as during any malfunction situation and any artifact images generated from the machine. Using their accumulated experience at solving machine malfunctions, the field engineer looks through the error log and the artifact images and tries to find any symptoms that may point to the fault. Then the field engineer tries to correct the problem that may be causing the machine malfunction. If the error log contains only a small amount of information, and the generated artifact images are well known, then this process will work fairly well. However, if the error log contains a large amount of imprecise information and the cause of the artifact images is unknown, as is usually the case for large complex devices, then it will be very difficult for the field engineer to quickly diagnose a fault. Therefore, there is a need for a system and method that can quickly diagnose a machine malfunction from a complex error log and artifact images having an unknown cause associated therewith.

Solutions to the problems described above have not heretofore included significant remote capabilities. Thus, there is a need for a medical diagnostic system which provides for the advantages of remote services and addresses the problems discussed above. In particular, there is a need for a system and method that can quickly diagnose a machine malfunction via a network. Further, there is a need for system structures, such as, a database and a diagnostic unit to be located in a remote service facility. Even further, there is a need to reduce the amount of equipment located at the image-based machine while maintaining the ability to quickly diagnose and service machine malfunctions.

SUMMARY OF THE INVENTION

One embodiment of the invention relates to a system for performing image-based diagnosis of a machine and includes a database containing a plurality of historical images taken from a plurality of machines, a diagnostic unit configured to diagnose a new artifact image from the machine and to communicate historical and non-historical images or data associated with the system to a remote facility. The plurality of historical images include a plurality of ideal images generated from the plurality of machines using all possible machine settings and a plurality of artifact images generated from the plurality of machines, each of the artifact images having known faults associated therewith and a corresponding corrective action for repairing the faults. The diagnostic unit includes a diagnostic image processor and a diagnostic fault isolator. The diagnostic image processor includes means for finding an ideal image from the plurality of historical images that most closely matches the new artifact image, means for assigning an artifact category to the new artifact image based on the matched ideal image, and means for extracting an artifact feature from the new artifact image according to the assigned category. The diagnostic fault isolator includes means for generating a plurality of metrics for the extracted artifact feature and means for applying the plurality of metrics to identify an artifact image from the plurality of historical images that most closely matches the new artifact image and a corrective action for repairing the unknown fault. The network provides remote services from the remote facility.

Another embodiment of the invention relates a method for performing image-based diagnosis of a machine. The method includes obtaining a plurality of historical images taken from a plurality of machines via a network; receiving a new artifact image from a machine having an unknown fault via the network; finding an ideal image from the plurality of historical images that most closely matches the new artifact image; assigning an artifact category to the new artifact image based on the ideal image that most closely matches the new artifact image; generating a plurality of metrics for the artifact category assigned to the new artifact image; and using the plurality of metrics to identify an artifact image from the plurality of historical images that most closely matches the new artifact image and a corrective action for repairing the unknown fault. The plurality of historical images include a plurality of ideal images generated from the plurality of machines using all possible machine settings and a plurality of artifact images generated from the plurality of machines, each of the artifact images having known faults associated therewith and a corresponding corrective action for repairing the faults.

Other principle features and advantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings, wherein like reference numerals denote like elements, and.

DETAILED DESCRIPTION OF THE PREFERRED EMBODIMENT

Figure 1:
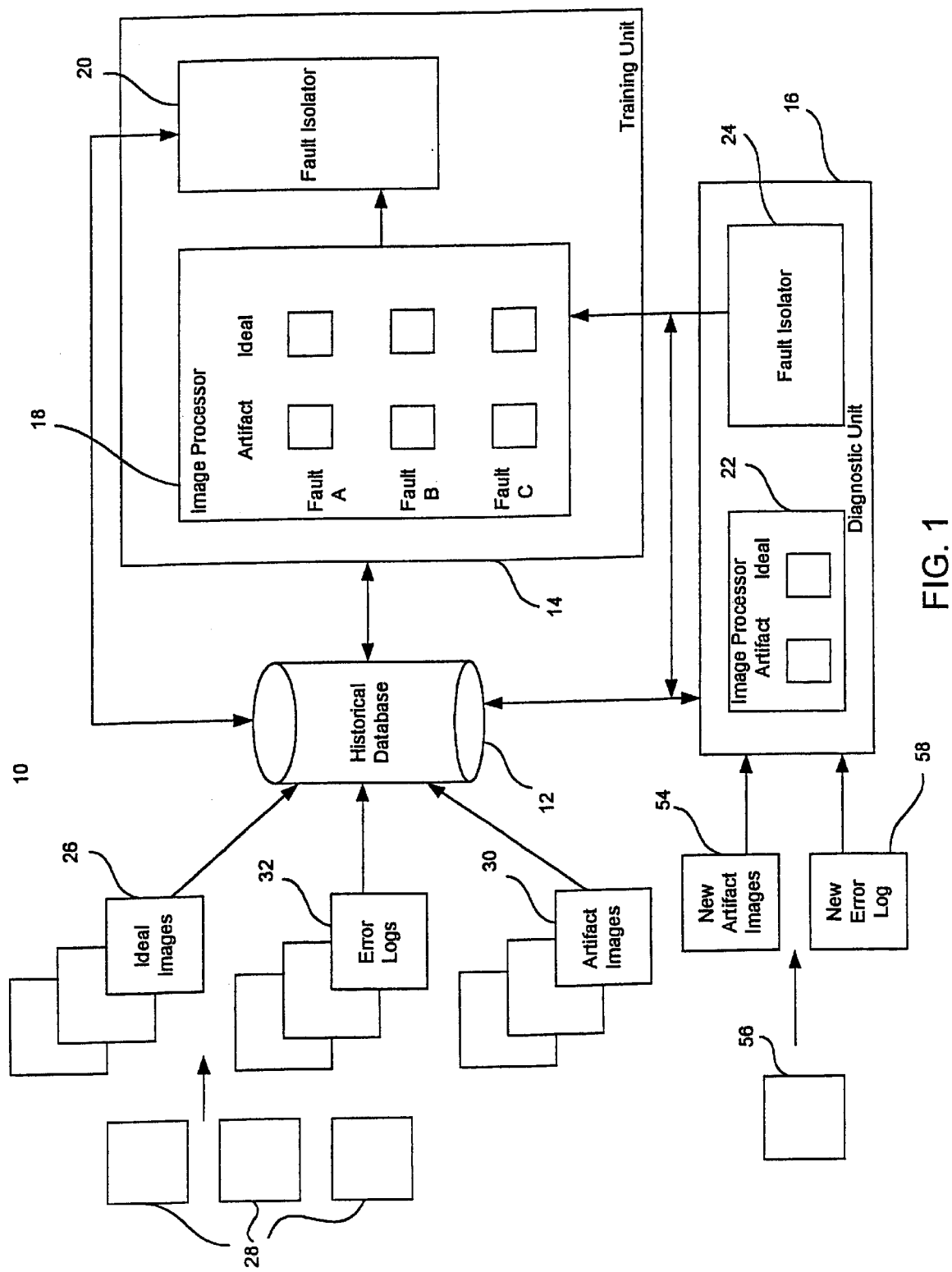
FIG. 1 shows a block diagram of an image-based diagnosis system according to a preferred embodiment.

The image-based diagnosis system of this invention is described with reference to a medical imaging device such as an ultrasound, CT, or MRI machine. Although this invention is described with reference to a medical imaging device, the image-based diagnosis system can be used in conjunction with any imaging device (chemical, mechanical, electronic, microprocessor controlled) which generates images. FIG. 1 shows a block diagram of an image-based diagnosis system 10 according to this invention. The image-based diagnosis system 10 includes a database 12 of historical images, a training unit 14, and a diagnostic unit 16. The training unit 14 includes an image processor 18 and a fault isolator 20. The diagnostic unit 16 also includes an image processor 22, and a fault isolator 24. Both the training unit 14 and the diagnostic unit 16 are embedded in a computer such as a workstation. However other types of computers can be used such as a mainframe, a minicomputer, a microcomputer, or a supercomputer.

The historical images stored in the database 12 comprise a plurality of ideal images 26 of phantoms generated from a plurality of imaging machines 28. The plurality of ideal images 26 of phantoms are generated from imaging machines using all possible probes and all possible machine default parameter settings. The model of the imaging machine, the probe used, the phantoms that were imaged, and the parameter settings on the imaging machines are inputted along with the ideal images into the database 12 remotely by a field engineer. Alternatively, the machine generating the images may be programmed to put this information in the image file itself, e.g., in the header of the image. Thus, the information becomes an integral part of the database 12. For images acquired remotely, the variables such as the model type, the probe used, and the phantom used, are present in the images themselves and can be automatically extracted later by the training unit 14. However, the parameter settings are not discrete and can potentially take on an infinite combination of continuous values. Accordingly, it is treated different than the other variables. In this invention, the number of machine settings are fixed to a finite set. For example, each ideal image that is acquired from the field is annotated by a field engineer or a technician on-site with the appropriate label specifying the parameter settings of the imaging machine. Examples of some of the parameter settings for an imaging machine are "abdominal setting", "thoracic setting", and "carotid setting".

In addition to a plurality of ideal images 26, the database 12 receives a plurality of artifact images 30 generated from the plurality of imaging machines 28. Each of the artifact images 30 are results of known faults such as unplugging a board, installing a defective board, etc. Like the ideal images 26, each of the artifact images 30 have variables accompanying it such as the model of the imaging machine, the probe used, the phantoms that were imaged, and the parameter settings on the imaging machines. Again the variables such as the model type, the probe used, and the phantom used are present in the images themselves and are automatically extracted, while the parameter settings variable is fixed to a finite set and specified by a field engineer or a technician. Also, the plurality of artifact images 30 and accompanying variables are inputted to the database 12 remotely by a field engineer. Alternatively, the machine generating the artifact images may be programmed to put this information in the image file itself, e.g., in the header of the image.

In addition to the plurality of artifact images 30, the database 12 receives a plurality of error logs and keyboard logs 32 generated from the imaging machines 28. The error logs and keyboard logs each contain a record of events of the imaging machines that occur during routine operation and any malfunction situation. The error logs and keyboard logs represent a signature of the operation of each imaging machine. Each of the error logs and keyboard logs 32 correspond to one of the artifact images 30. For example, one of the error logs and keyboard logs might contain a sequence of events for an imaging machine that has a board unplugged. Another error log and keyboard log might contain a sequence of events for an imaging machine that was installed with a defective board. The plurality of error logs and keyboard logs 32 are stored in the database 12 and are used as historical cases documenting the software and hardware errors occurring at the different imaging machines 28. A description of the processing of the historical cases is described later in more detail.

After the plurality of artifact images 30 and error logs and keyboard logs 32 have been inputted to the database 12, the artifact images are partitioned into a plurality of sets. In particular, the artifact images 30 are partitioned into MxPxFxS sets, wherein M is the number of imaging machines, P is the number of probes, F is the number of phantoms available, and S is the number of machine settings. Since some of the machines cannot handle all of the probes or machine settings there will be some empty sets. Partitioning the artifact images 30 into sets makes it easier to find a historical match for a new artifact image having an unknown fault.

Figure 2:
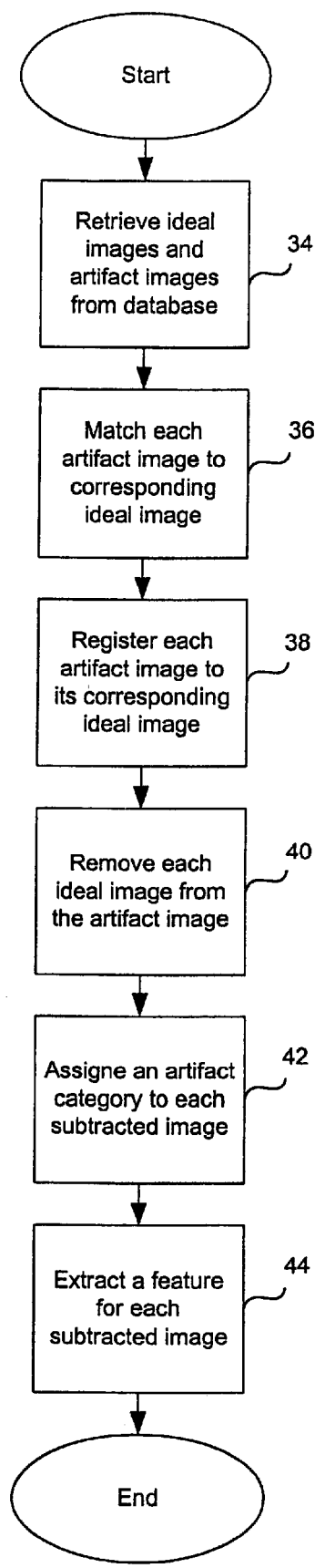
FIG. 2 shows a flow chart setting forth the image processing steps performed by the training unit shown in FIG. 1.

The historical images in the database 12 are accessed by the training unit 14 through the image processor 18. The image processor 18 processes the plurality of ideal images 26 with the plurality of artifact images 30. FIG. 2 shows a flow chart setting forth the image processing steps performed by the image processor 18. The image processing steps begin at 34 where the plurality of ideal images 26 and plurality of artifact images 30 are retrieved from the database 12. Each artifact image is then matched to a corresponding ideal image at 36. The matching process ensures that the machine type, probe, and machine settings are the same for the artifact and ideal images.

For each match, the artifact image is then registered to its corresponding ideal image at 38. Typically, the images are acquired manually by placing a probe from the imaging machine onto a phantom. A result of the manual placement of the probe is that the there is a certain variability in the images from one acquisition to the next. Registration is used to remove the variability as much as possible. Any residual misregistration that remains after registration is taken into account later by the categorization step which is described below. Essentially, the registration enables a pixel by pixel comparison of images acquired at different times. In this invention, registration is achieved by mapping the artifact image to the ideal image. This entails specifying fiducial markers in the artifact images. The image processor 18 then processes the regions of interest covered in the fiducial markers to derive a two-dimensional point that can be matched with the corresponding ideal image. More specifically, the image processor 18 takes the centroid of each fiducial marker and uses it to do point to point matching with the ideal image. Alternatively, it is possible to carry out registration by warping the artifact image to the corresponding ideal image so that there is maximum correlation. The warping may be done via a perspective, affine, or rigid body transformation of one image to match the other image.

After registration, each ideal image is removed from the artifact image at 40. In this invention, the ideal image is removed by using a subtraction operation. The subtraction operation is done pixel by pixel, whereby the gray-level of the ideal image pixel is taken out from that of the artifact image. Since the final image may contain negative numbers after this operation, the subtracted image is renormalized such that the minimum pixel in it is zero. The subtraction operation results in a subtracted image that contains only the artifacts. Alternatively, a filtration operation may be applied to both images before subtraction to account for any residual misregistration between the ideal images and the artifact images.

After subtraction, an artifact category is then assigned to each subtracted image at 42. In this invention, the assigned artifact category is based on an eigen space representation of the subtracted artifact images. The eigen space representation is determined by first computing a covariance matrix. To determine the covariance matrix, each subtracted image is represented by a vector V of pixel values. For an nxm image, the first n values are the n pixels in the first row of the image, the next n values are the pixel values in the second row of the image, and so forth. The given set of N subtracted images are represented by $[V_1, V_2, \ldots V_N]$. The average of all of the subtracted images is represented by $V_{avg}$. The covariance matrix is defined by the following equation:

$$\text{cov}[i, j] = \frac{|V_i - V_{avg}| \cdot |V_j - V_{avg}|}{nxm}, \text{ wherein} \quad (1)$$

$i, j \in [1, 2, \ldots N]$ and "·" denotes the dot product.

After the covariance matrix has been determined, it is used to obtain an orthogonal representation and an image basis. The orthogonal representation and image basis are attained by performing a Singular Value Decomposition (SVD) on the covariance matrix. Alternatively, a Karhunen-Loeven Transform (KLT) can be used to determine the orthogonal representation and image basis. The KLT is the statistical equivalent of the SVD and entails diagonalization of the covariance matrix. For a KLT, the covariance matrix is represented by Q and is defined as:

$$Q = UDV^T, \text{ wherein} \quad (2)$$

U and V are orthonormal and D is a diagonal matrix. The columns of V define a new image basis. It is a property of this new basis set that the images in it are uncorrelated. Other less computationally intensive methods may be used to obtain the orthogonal representation and image basis. For example, a discrete cosine transform (DCT) may be used.

The determined image basis is then used to find a representation for each of the subtracted artifact images. In particular, each of the subtracted artifact images are represented as a linear combination of the images in the new basis set. Thus, if $B_1, B_2, \ldots B_N$ are the N basis images, then a historical artifact image I is characterized by the coefficients $\alpha_1, \alpha_2, \ldots \alpha_n$, such that $$I = \alpha_1 B_1 + \ldots + \alpha_N B_N, \text{ wherein} \quad (3)$$

$[\alpha_1, \ldots \alpha_N]$ is a point in the N dimensional space defined by $[B_1, \ldots B_N]$. Each subtracted artifact image in the historical database is represented by one such point. After a representation is found for each of the subtracted artifact images, then clusters of closely spaced points in this hyperspace are designated as artifact categories. Some possible examples of designated artifact categories, for the ultrasound imaging modality, are "Flash light artifacts", "TD board artifacts", "Search light artifacts", and "Distortion artifacts". These examples are illustrative of some of the types of artifact categories that may be used in this invention and is not meant to be exhaustive. For illustration purposes, some of the artifact categories are shown in FIG. 1 as Fault A, Fault B, and Fault C.

After categorization, the image processor 18 extracts a set of artifact features for each of the artifacts at 44. Artifact features are extracted by first converting each artifact image generated from the subtraction operation into the Fourier domain. Converting the artifact images into the Fourier domain results in a spectral signature of the artifacts. Many category-specific features that can be measured, include image homogeneity, signal-to-noise ratio, modulation transfer function, resolution, distortion, signal attenuation, and texture properties. This invention is not limited to these category-specific features and other features can be measured if desired.

Figure 3:
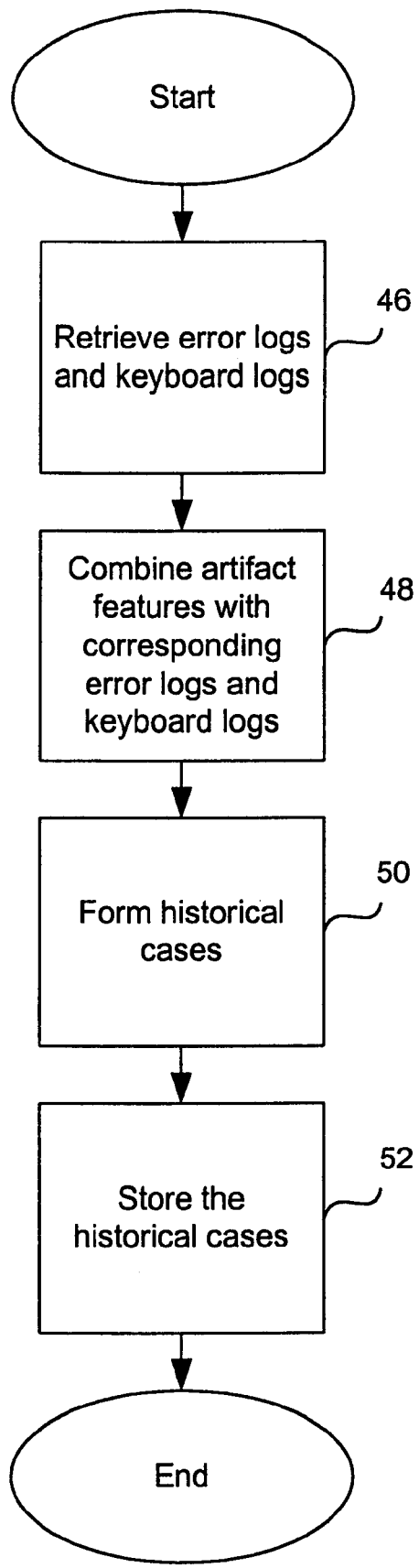
FIG. 3 shows a flow chart setting forth the fault isolation processing steps performed by the training unit shown in FIG. 1.

Referring back to FIG. 2, after the artifact features for all of the artifact images have been determined, the image processor 18 sends the features to the fault isolator 20 for further processing. FIG. 3 shows a flow chart setting forth the processing steps performed by the fault isolator 20. The fault isolator 20 first retrieves the error logs and keyboard logs 32 from the database 12 at 46. Next, the error logs and keyboard logs 32 are combined with their corresponding artifact features at 48. The features of each artifact, which have been quantified using various category-specific metrics typify the syndrome associated with an actual fault. The error logs and keyboard logs also typify the syndrome associated with the actual fault. These three sources of information are used to generate a case for a case-based reasoning system. Each set of combined artifact features and logs generates a historical case at 50. The historical cases of artifact features and logs are then stored in the database at 52 and used later by the diagnostic unit 16 to diagnose a new problem situation in which there is a new artifact image generated from an imaging machine having an unknown fault.

Referring back to FIG. 1, the diagnostic unit 16 receives a new artifact image 54 generated from an imaging machine 56 experiencing an unknown fault. In addition, a new error log and keyboard log 58 of the events occurring at the imaging machine 56 is sent to the diagnostic unit 16. Both the new artifact image 54 and the new error log and keyboard log 58 are inputted to the diagnostic unit 16 at its image processor 22 by either a field engineer or by a remote dial-in connection. The image processor 22 processes the new artifact image 54 and new error log and keyboard log 56 with the historical cases stored in the database 12.

Figure 4:
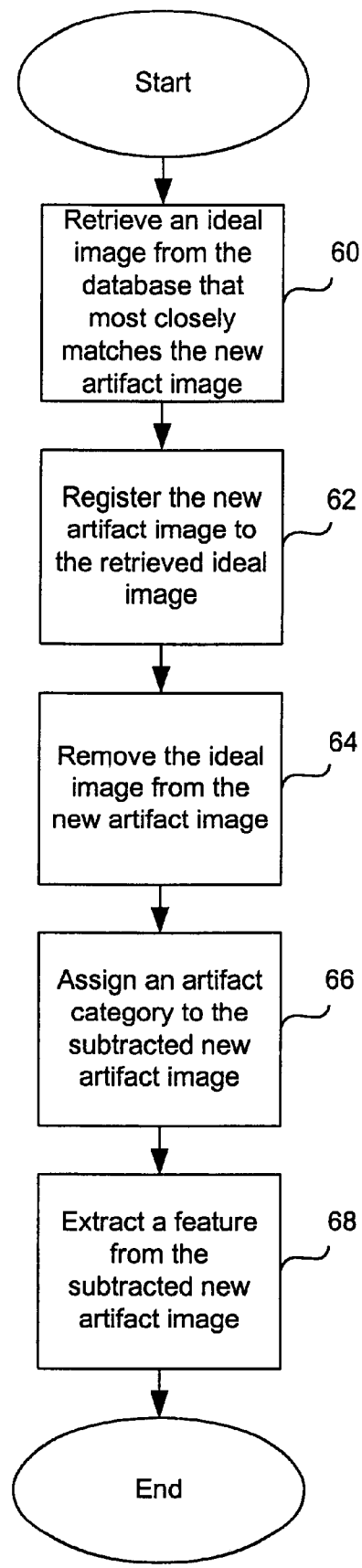
FIG. 4 shows a flow chart setting forth the image processing steps performed by the diagnostic unit shown in FIG. 1.

FIG. 4 shows a flow chart setting forth the image processing steps performed by the image processor 22. After acquiring the new artifact image, the image processor 22 then searches the database 12 and retrieves an ideal image that most closely matches the new artifact image at 60. The image processor then registers the ideal image to the new artifact image at 62. As mentioned above, registration is achieved by mapping the new artifact image to the ideal image by specifying fiducial markers in the new artifact image and processing the markers to derive a two-dimensional point that is matched with the ideal image. After registration, the ideal image is then subtracted from the new artifact image at 64 by using a subtraction or filtration operation. The subtracted image is represented as a linear combination of the same basis set $[B_1, \ldots B_N]$ and is defined as:

$$I_{artifact} = \beta_1 B_1 + \ldots + \beta_N B_N, \text{ wherein} \quad (4)$$

the point $\{\beta V1, \ldots \beta_N\}$ represents another point in the space of historical artifact images. The distance of this point from all of the artifact clusters is used to determine which category the incoming image belongs to. An artifact category is then assigned to the subtracted new artifact image at 66. After an artifact category has been assigned, an artifact feature is then extracted from the subtracted new artifact image at 68 by the image processor 22 in the manner described above.

Figure 5:
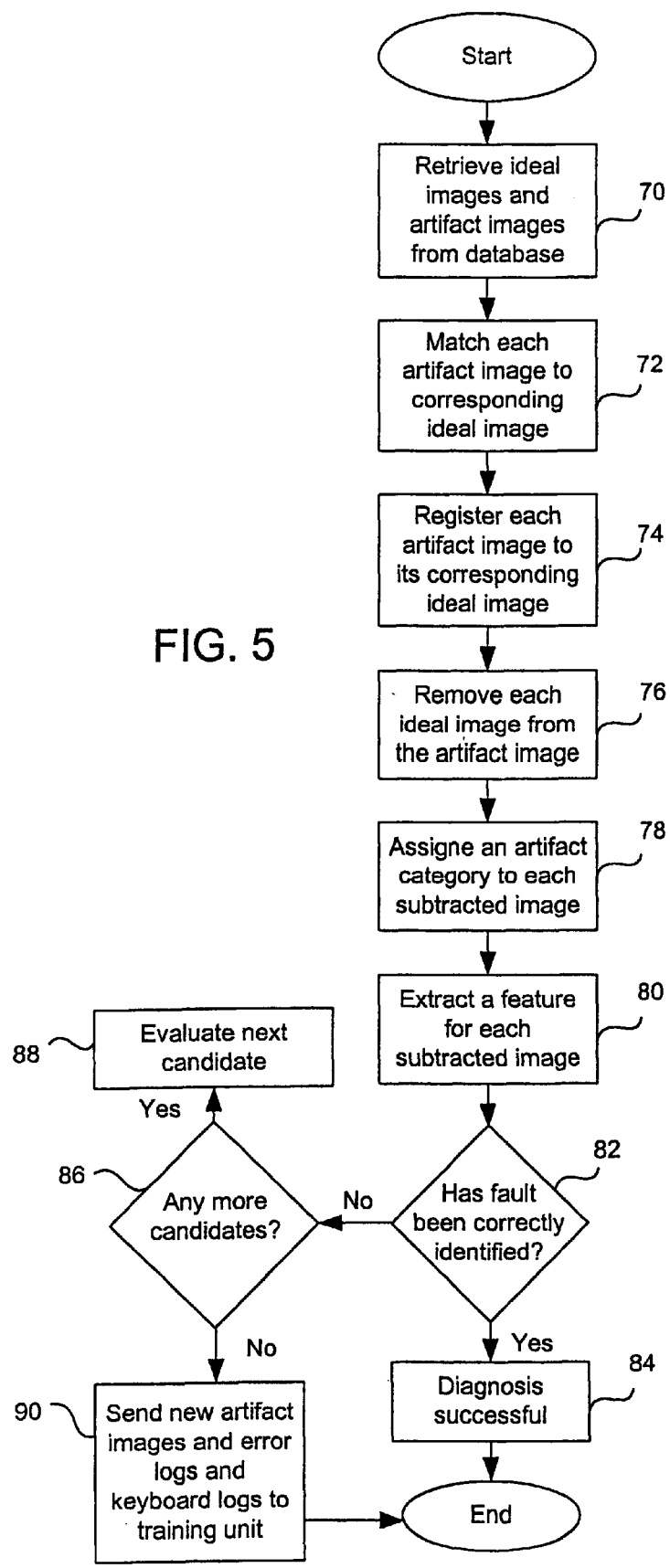
FIG. 5 shows a flow chart setting forth the fault isolation processing steps performed by the diagnostic unit shown in FIG. 1.

After the artifact feature for the new artifact image has been determined, the image processor 22 sends the feature to the fault isolator 24 for further processing. FIG. 5 shows a flow chart setting forth the processing steps performed by the fault isolator 24. The fault isolator 24 uses the extracted artifact feature to generate category specific metrics at 70. The metrics are used to further typify the fault that causes the imaging machine 56 to produce the artifact image 54. Next, the error log and keyboard log 58 accompanying the new artifact image 54 are retrieved at 72. The fault isolator 24 then searches the historical cases in the database 12 at 74 for cases that most likely match the new artifact image. A candidate set of images that most likely match the new artifact image are generated at 76. In addition, corrective actions for repairing the faults corresponding to each of the candidates are retrieved at 78. One type of corrective action may be identifying the field replaceable unit within the imaging machine 56 that needs to be replaced.

The candidate set of images and corresponding corrective actions are ranked in order of their likelihood of matching the new artifact image and presented to a field engineer at 80. The field engineer then goes through the candidate sets in the ranked order at 82 and determines if the fault resulting in the new artifact image has been correctly identified. If the fault has been correctly identified, then the fault isolator 24 logs the diagnosis as successful at 84. On the other hand, if the fault has not been correctly identified, then it is determined whether there are any more candidate sets to evaluate at 86. If there are more candidates, then the next candidate is evaluated at 88 and 82 again. These steps continue until the fault has been correctly identified. However, if none of the candidates correct the fault, then the new artifact image 54 and error log and keyboard log 58 are sent to the training unit 14 at 90 and added to the historical cases for diagnosing future faults. Eventually, as more cases are added to the training unit 14, the image-based diagnosis system's level of accuracy will even out and then it will be unnecessary to add any more cases to the training unit.

Figure 6:
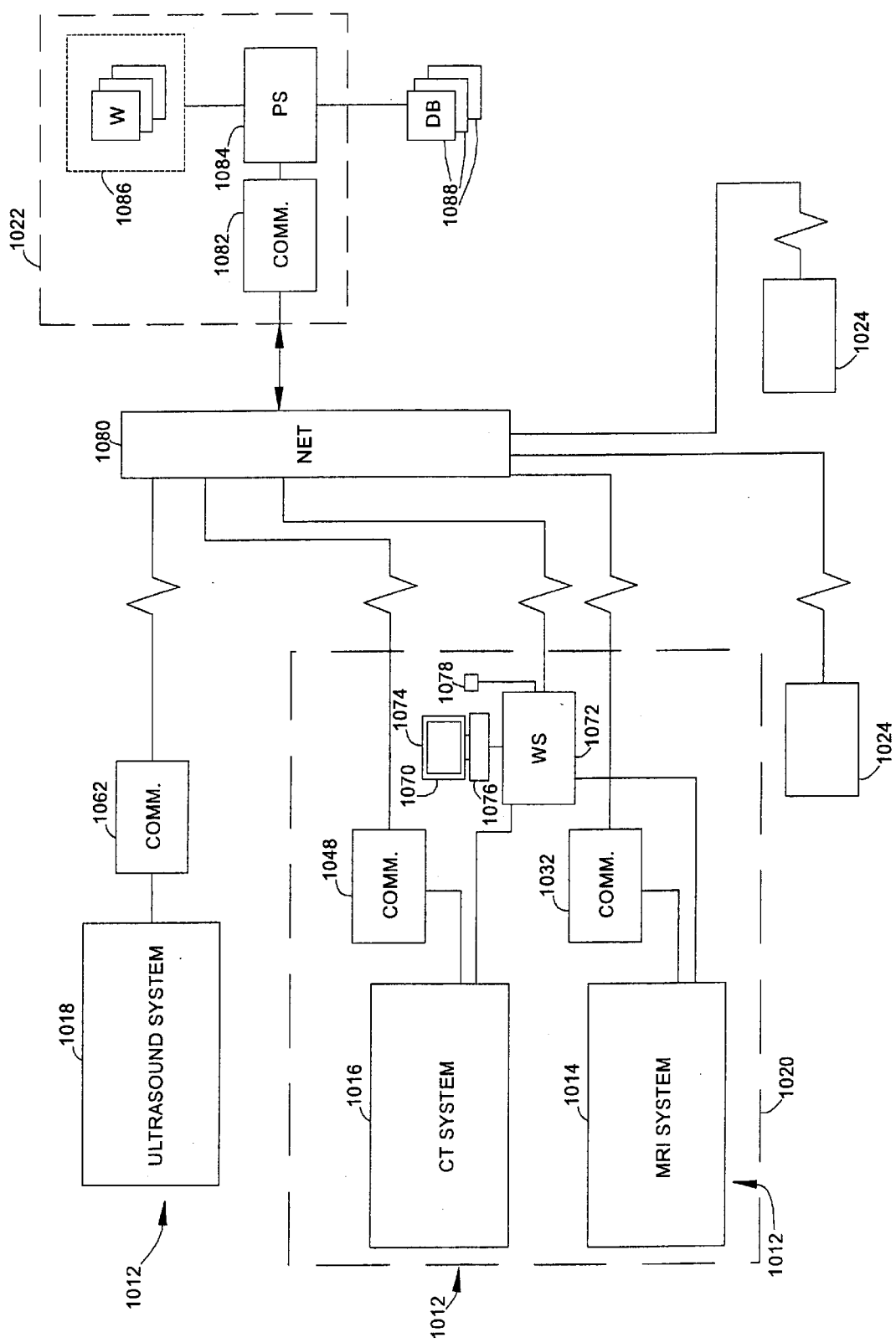
FIG. 6 is a diagrammatical representation of a series of medical diagnostic systems coupled to a service facility via a network connection for providing remote services and data interchange between the diagnostic systems and the service facility.

Referring now to FIG. 6, a service system 1010 is illustrated for providing remote service to a plurality of medical diagnostic systems 1012, including systems such as image-based diagnosis system 10 illustrated in FIG. 1. In the embodiment illustrated in FIG. 6, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 6, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors. In general, however, the present technique is particularly well suited to providing remote service to a wide variety of medical diagnostic system modalities, including MRI systems, CT systems, ultrasound systems, positron emission tomography (PET) systems, nuclear medicine systems, and so forth. Moreover, the various modality systems serviced in accordance with the present techniques may be of different type, manufacture, and model.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 6, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain types of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 6. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 7:
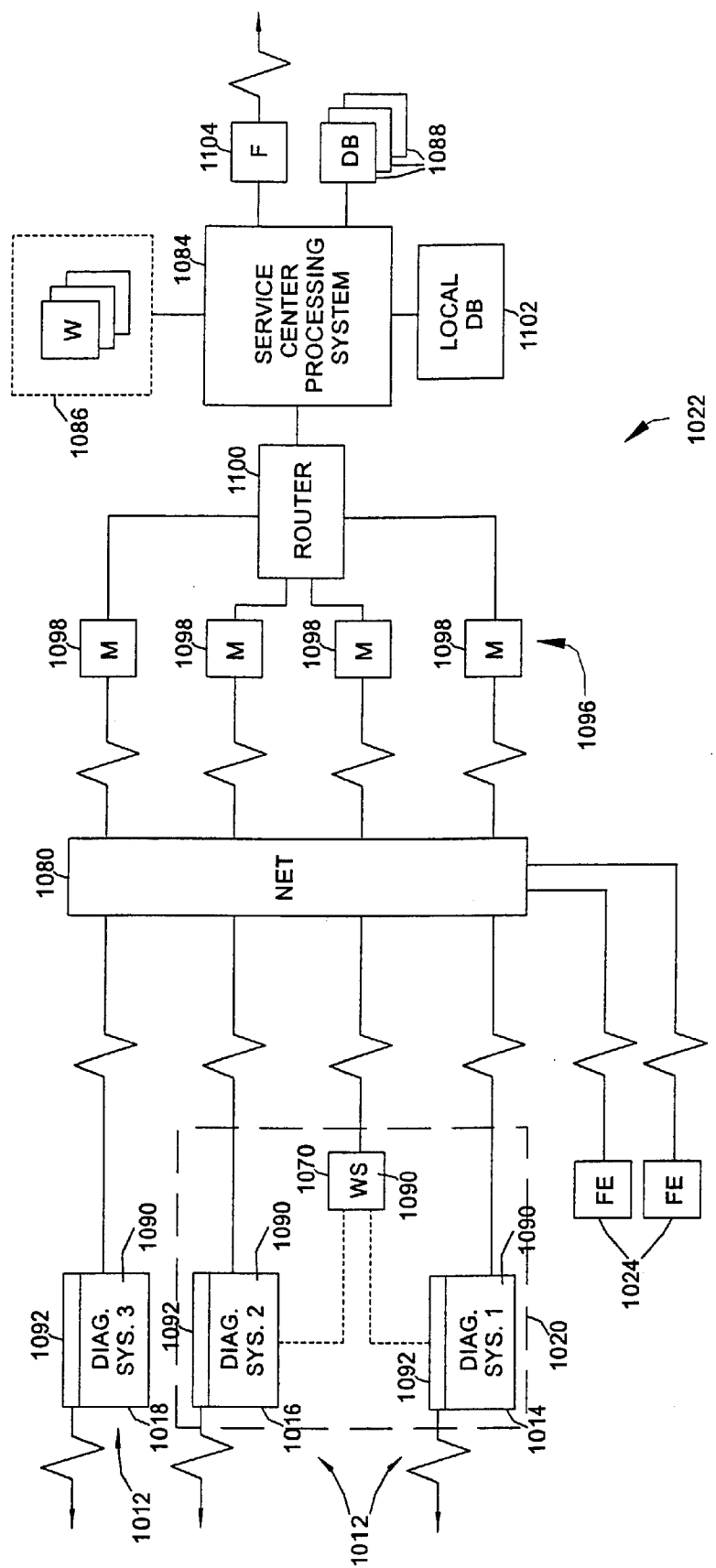
FIG. 7 is a block diagram of the systems shown in FIG. 6 illustrating certain functional components of the diagnostic systems and the service facility.

FIG. 7 is a block diagram illustrating the foregoing system components in a functional view. As shown in FIG. 7, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 8, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 7, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 8:
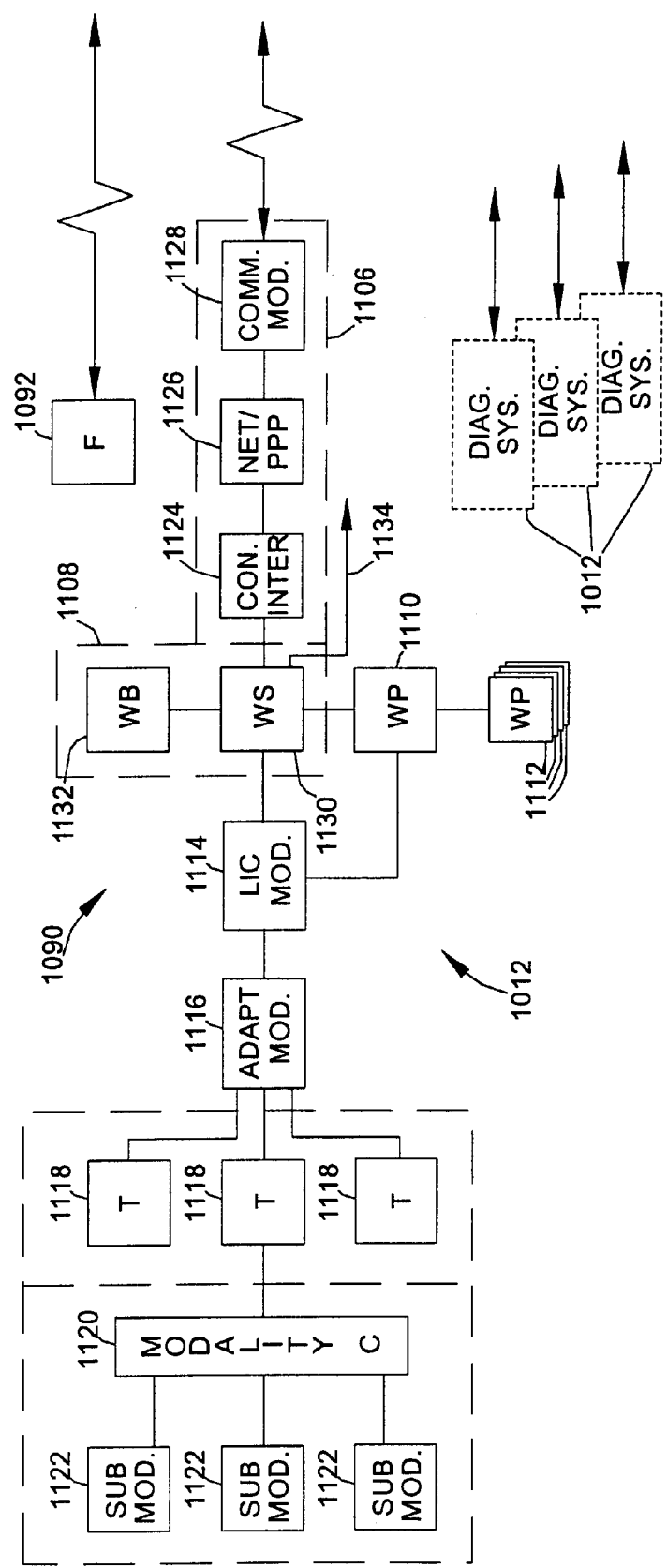
FIG. 8 is a block diagram of certain functional components within a diagnostic system of the type shown in FIGS. 6 and 7 for facilitating interactive remote servicing of the diagnostic system.

FIG. 8 illustrates diagrammatically the various functional components comprising the uniform service platform 1090 within each diagnostic system 1012. As shown in FIG. 8, the uniform platform includes a device connectivity module 1106, as well as a network connectivity module 1108. Network connectivity module 108 accesses a main web page 110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 6 and 7).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 9:
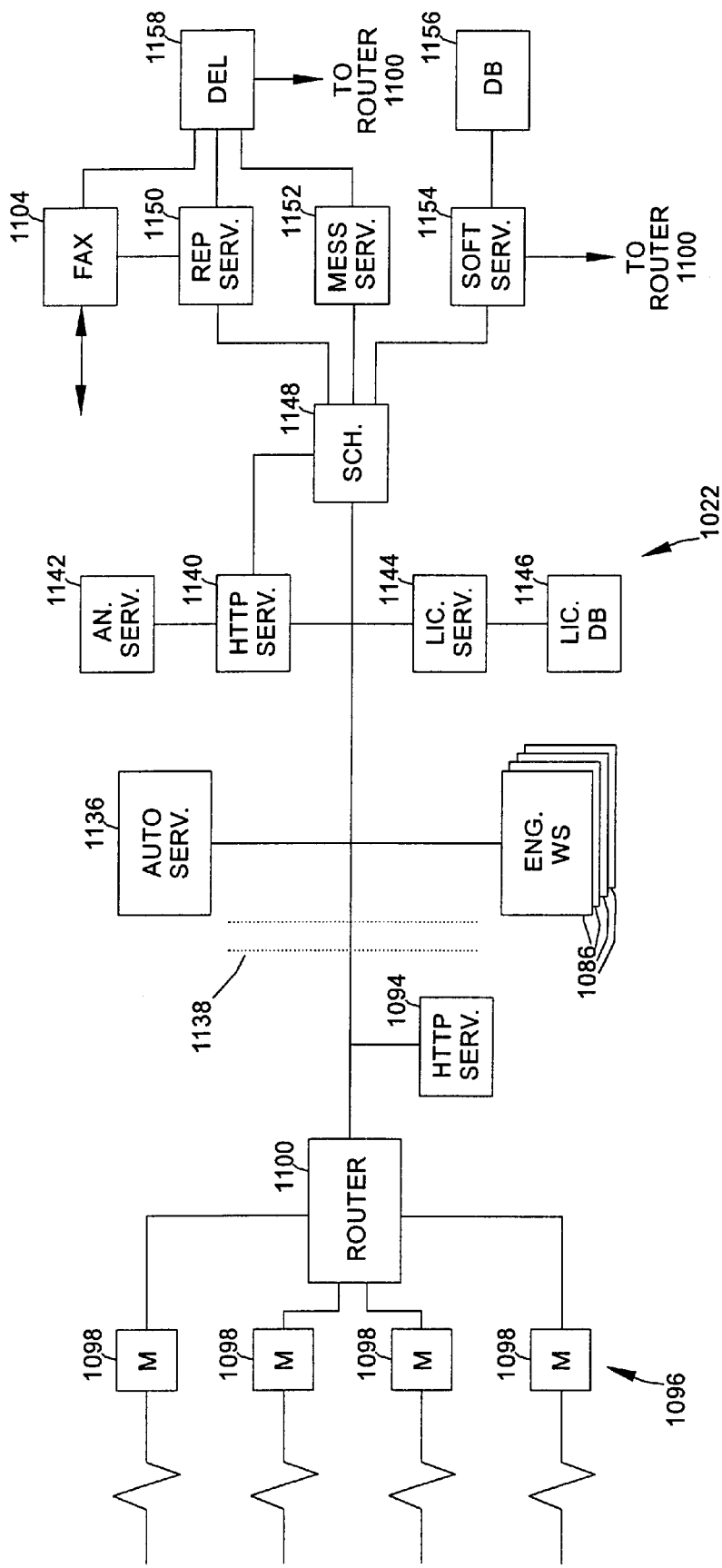
FIG. 9 is a block diagram of certain of the functional components of the service facility illustrated in FIGS. 6 and 7 for rendering interactive remote service to a plurality of medical diagnostic systems.

FIG. 9 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 9, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1154 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 6) provides remote services, such as, remote diagnostics, remote control, remote monitoring, remote file storage, and remote servicing. Advantageously, service system 1010 (FIG. 6) allows image-based diagnosis system 10 to locate any one of database 12, training unit 14, and diagnostic unit 16 in a remote facility, such as in the present instance, service facility 1022. As such, image-based diagnosis system 10 (FIG. 1) incorporated into service system 1010 (FIG. 6), includes the capability of quick diagnostic and service functions, as described herein, while avoiding the necessity of having local equipment, such as, database 12, training unit 14, and diagnostic unit. Such equipment may be located in at least one remote facility. Multiple image-based diagnosis systems may then cooperate to share high capacity databases and high speed processing units for diagnostic and service functions.

While the embodiments illustrated in the Figures and described above are presently preferred, it should be understood that the embodiments are offered by way of example only. Other embodiments may include, for example, processing units which provide expedited remote correction to machines having unknown faults and coupled to a communication network. The invention is not limited to a particular embodiment, but extends to various modifications, combinations, and permutations that nevertheless fall within the scope and spirit of the appended claims.

What is claimed is:

1. A system for performing image-based diagnosis of a machine, comprising:

a database containing a plurality of historical images taken from a plurality of machines, the plurality of historical images comprising a plurality of ideal images generated from the plurality of machines using all possible machine settings and a plurality of artifact images generated from the plurality of machines, each of the artifact images having known faults associated therewith and a corresponding corrective action for repairing the faults; and a diagnostic unit configured to diagnose a new artifact image from the machine, the machine having an unknown fault, the diagnostic unit being further configured to communicate historical and non-historical images or data associated with the system to a remote facility, the diagnostic unit comprising a diagnostic image processor comprising means for finding an ideal image from the plurality of historical images that most closely matches the new artifact image, means for assigning an artifact category to the new artifact image based on the matched ideal image, and means for extracting an artifact feature from the new artifact image according to the assigned category; and a diagnostic fault isolator comprising means for generating a plurality of metrics for the extracted artifact feature and means for applying the plurality of metrics to identify an artifact image from the plurality of historical images that most closely matches the new artifact image and a corrective action for repairing the unknown fault.

2. The system according to claim 1, further comprising a training unit coupled to the database and the diagnostic unit, the training unit comprising a training image processor comprising means for obtaining the plurality of artifact images and the plurality of ideal images, means for matching each of the plurality of artifact images to a corresponding ideal image, means for assigning an artifact category to each match, and means for extracting an artifact feature from each match according to the assigned category.

3. The system according to claim 2, wherein the training image processor further comprises means for registering the artifact image with its known fault to the corresponding ideal image and means for removing the corresponding ideal image from the registered image.

4. The system according to claim 2, wherein the training unit further comprises a training fault isolator coupled to the training image processor for isolating the extracted artifact features into historical cases.

5. The system according to claim 4, wherein the database further comprises a plurality of error logs generated from the plurality of machines, each of the plurality of error logs containing data representative of events occurring during operation of the machines.

6. The system according to claim 5, wherein the training fault isolator combines the extracted artifact features and error logs into historical cases.

7. The system according to claim 1, wherein the diagnostic image processor further comprises means for registering the new artifact image to the matched ideal image and means for removing the corresponding ideal image from the registered image.

8. The system according to claim 1, wherein the diagnostic fault isolator comprises means for receiving an error log generated from the machine having the unknown fault, the error log containing data representative of events occurring during operation of the machine.

9. The system according to claim 8, wherein the diagnostic fault isolator uses the error log to generate the plurality of metrics.

10. The system according to claim 1, wherein the diagnostic unit further comprises means for adding newly identified artifact images and corresponding corrective actions to the plurality of artifact images in the database.

11. The system according to claim 1, further comprising means for servicing the machine having the unknown fault.

12. A method for performing image-based diagnosis of a machine, comprising the steps of:
obtaining a plurality of historical images taken from a plurality of machines via a network, the plurality of historical images comprising a plurality of ideal images generated from the plurality of machines using all possible machine settings and a plurality of artifact images generated from the plurality of machines, each of the artifact images having known faults associated therewith and a corresponding corrective action for repairing the faults;
receiving a new artifact image from a machine having an unknown fault via the network;
finding an ideal image from the plurality of historical images that most closely matches the new artifact image;
assigning an artifact category to the new artifact image based on the ideal image that most closely matches the new artifact image;
generating a plurality of metrics for the artifact category assigned to the new artifact image; and
using the plurality of metrics to identify an artifact image from the plurality of historical images that most closely matches the new artifact image and a corrective action for repairing the unknown fault.

13. The method according to claim 12, wherein the step of obtaining the plurality of historical images comprises the steps of:
matching each of the plurality of artifact images to a corresponding ideal image taken from the plurality of ideal images;
assigning an artifact category to each match; and
extracting an artifact feature from each match.

14. The method according to claim 13, further comprising the steps of:
registering the artifact image with its known fault to the corresponding ideal image; and
removing the corresponding ideal image from the registered image.

15. The method according to claim 12, further comprising the step of determining an artifact feature for the new artifact image.

16. The method according to claim 12, further comprising the steps of:
registering the new artifact image to a corresponding ideal image; and
removing the corresponding ideal image from the registered image.

17. The method according to claim 12, further comprising the step of adding newly identified artifact images and corresponding corrective actions to the plurality of artifact images in the plurality of historical images.

18. The method according to claim 12, further comprising the step of inputting an error log from the machine having the unknown fault, the error log containing data representative of events occurring during operation of the machines.

19. The method according to claim 18, wherein the inputted error log is used to generate the plurality of metrics for new artifact image.

20. The method of claim 12, further comprising communicating a corrected image to the machine having the unknown fault via the network.

21. The method of claim 20, further comprising providing the corrected image to an operator workstation.

* * * * *